United States Patent
Kilty et al.

(10) Patent No.: US 8,975,031 B2
(45) Date of Patent: Mar. 10, 2015

(54) METHOD FOR PREDICTING A NEED FOR RENAL REPLACEMENT THERAPY (RRT)

(71) Applicant: Argutus Intellectual Properties Limited, Dublin (IE)

(72) Inventors: Cormac Gerard Kilty, Sandycove (IE); Jay Lawrence Koyner, Chicago, IL (US); Claire Victoria McGrath, Dun Laoghaire (IE); Patrick Thomas Murray, Chicago, IL (US); Kerstin Schuster, Blackrock (IE)

(73) Assignee: Argutus Intellectual Properties Limited

(*) Notice: Subject to any disclaimer, the term of this patent is extended or adjusted under 35 U.S.C. 154(b) by 0 days.

(21) Appl. No.: 13/866,540

(22) Filed: Apr. 19, 2013

(65) Prior Publication Data
US 2013/0236908 A1   Sep. 12, 2013

Related U.S. Application Data

(60) Continuation of application No. 12/959,546, filed on Dec. 3, 2010, now abandoned, which is a division of application No. 12/076,410, filed on Mar. 18, 2008, now abandoned.

(51) Int. Cl.
*G01N 33/53* (2006.01)
*G01N 33/68* (2006.01)

(52) U.S. Cl.
CPC .. *G01N 33/6893* (2013.01); *G01N 2333/91177* (2013.01); *G01N 2800/347* (2013.01)
USPC ............................................ 435/7.1; 435/7.2

(58) Field of Classification Search
None
See application file for complete search history.

(56) References Cited

U.S. PATENT DOCUMENTS

2004/0219603 A1   11/2004   Devarajan et al.

OTHER PUBLICATIONS

Sundberg et al. Nephron 1994 vol. 67, p. 308-316.*
Arici et al., "Radiocontrast-induced nephrotoxicity and urinary alpha-glutathione S-transferase levels: Effect of amlodipine administration", Int'l Urology & Nephrology, vol. 35, 2003, pp. 255-261.
Bagshaw et al., "Urinary biomarkers in septic acute kidney injury", Intensive Care Med., vol. 33, 2007, pp. 1285-1296.
Biotrin Biomarkers, Biotrin's Clinical Kidney Biomarkers, Biotin International, Dublin, Ireland, pp. 1-12. (www.biotrin.com).
Boldt et al., "Kidney-Specific Proteins in Elderly Patients Undergoing Cardiac Surgery with Cardiopulmonary Bypass", Anesth Analg., vol. 97 (2003) pp. 1582-1589.
Branten et al., "Urinary Excretion of Gluthathione S Transferases Alpha and Pi in Patients with Proteinuria: Reflection of the Site of Tubular Injury", Nephron, vol. 85, 2000, pp. 120-126.
Davis et al., "Acute Renal Failure after Cardiopulmonary Bypass is Related to Decreased Serum Ferritin Levels", Journal of the American Society of Nephrology, vol. 1, 1999, pp. 2396-2402.
Eijkenboom et al., "Small increases in the urinary excretion of glutathione S-transferase A1 and P1 after cardiac surgery are not associated with clinically relevant renal injury", Intensive Care Medicine, vol. 31, 2005, pp. 664-667.
Fervenza et al., "Induction of Heme Oxygenase-1 and Ferritin in the Kidney in Warm Antibody Hemolytic Anemia", Am. J. Kidney Diseases, vol. 52, No. 5, Nov. 2008, pp. 972-977.
Herget-Rosenthal et al., "Prognostic Value of Tubular Proteinuria and Enzymuria in Nonoliguric Acute Tubular Necrosis", Clinical Chemistry, vol. 50, No. 3 (2004) pp. 552-558.
Koyner et al., "Urinary Cystatin C and Neutrophil Gelatinase-Associated Lipocalin (NGAL) in Patients with Acute Kidney Injury Following Adult Cardiac Surgery", American Society of Nephrology, Renal Week 2007, Oct. 31-Nov. 5, 2007.
Lassnigg et al., "Minimal Changes of Serum Creatinine Predict Prognosis in Patients after Cardiothoracic Surgery: A Prospective Cohort Study", Journal of the American Society of Nephrology, vol. 15, 2004, pp. 1597-1605.
Mangano et al., "Renal Dysfunction after Myocardial Revascularization: Risk Factors, Adverse Outcome, and Hospital Resource Utilization", Multicenter Study of Perioperative Ischemia Research Group, Feb. 1, 1998; vol. 128 Issue 3; pp. 194-203.
Mehta et al., "Acute Renal Failure and Cardiac Surgery: Marching in Place of Moving Ahead?", J. Am. Soc. Nephrol., vol. 16, (2005), pp. 12-14.
PCT International Search Report and Written Opinion cited in PCT/IE2008/000057, on May 6, 2008.
Tuttle et al., "Predictors of ARF After Cardiac Surgical Procedures", American Journal of Kidney Diseases, vol. 41, No. 1; Jan. 2003: pp. 76-83.
Westhuyzen et al., "Measurement of tubular enzymuria facilitates early detection of acute renal impairment in the intensive care unit", Nephrol. Dial. Transplant, vol. 18, 2003, pp. 543-551.

* cited by examiner

*Primary Examiner* — Jacob Cheu
(74) *Attorney, Agent, or Firm* — Birch, Stewart, Kolasch & Birch, LLP.

(57) ABSTRACT

A method for predicting a need for Renal Replacement Therapy (RRT) in a patient comprises: determining a concentration of pi glutathione S transferase-($\pi$GST) in a first urine sample from the patient; and wherein a need for RRT is predicted when the $\pi$GST concentration is determined to be elevated in comparison to a patient without kidney injury. The method according to the invention can further comprise detecting for the presence of risk factors for RRT in a patient, the risk factors including elevated serum creatinine concentration, type I diabetes, type II diabetes, hypertension, dyslipidemia, hyperglycaemia, proteinuria and hypoalbuminemia.

9 Claims, 6 Drawing Sheets

METHOD FOR PREDICTING A NEED FOR RENAL REPLACEMENT THERAPY (RRT)

CROSS REFERENCE TO RELATED APPLICATIONS

This application is a Continuation of copending application Ser. No. 12/959,546 filed on Dec. 3, 2010, which is a Divisional of abandoned application Ser. No. 12/076,410 filed on Mar. 18, 2008. The entire contents of all of the above applications are hereby incorporated by reference.

TECHNICAL FIELD

This invention relates to the early identification and prediction of kidney damage, including early identification and prediction of elevated blood creatinine levels resulting from a reduction in kidney function in a subject and, in particular, to biomarkers for the detection thereof.

BACKGROUND ART

There are many causes of a reduction in kidney function and it is essential that corrective action is taken as early as possible by appropriate medical intervention so as to minimise as far as possible the deleterious consequences, which include total renal failure and a need for dialysis and ultimately kidney transplant. For example, an abrupt reduction in kidney function occurs frequently following cardiothoracic (CT) surgery. Thus, Acute Kidney Injury (AKI) is common following CT surgery occurring in 7-42% of patients (Mora Mangano, C. et al (1998) Ann Intern Med 128:194-203; and Tuttle, K. R. et al (2003) Amer J. Kid Dis 41:76-83.) Small changes in serum creatinine have been shown to correlate with increased morbidity and mortality, following CT surgery (Lassnigg, A. et al (2004) J. Am Soc Nephrol 15; 1597-1605).

Measurement of creatinine is the standard test in the clinic for measuring kidney function. If kidney function is abnormal, creatinine levels will increase in the blood due to decreased excretion of creatinine in the urine. Creatinine levels vary according to a person's age, size and muscle mass. In acute conditions build up of creatinine in the blood may take up to 24-72 hours to occur.

Patients who develop severe AKI requiring Renal Replacement Therapy (RRT), after CT surgery have a greatly increased in-hospital mortality (63%) compared to those with non-dialyzed AKI (19%), or stable renal function (0.9%) (Mora Mangano, C. et al (1998) supra).

Koyner, J. L. et al (poster presentation at American Society of Nephrology, Renal Week 2007, Oct. 31-Nov. 5, 2007, Moscone Center, San Francisco, Calif.) have investigated urinary Cystatin C (CyC) and Neutrophil Gelatinase—Associated Lipocalin (NGAL) in patients with AKI following adult cardiac surgery. Koyner, J L et al found that urinary CyC excretion increases in the early post-operative period following adult CT surgery and concluded that urinary CyC may be a useful early biomarker for the development of AKI as it appears to correlate with the severity of AKI and thus the future need of RRT. Similarly, Koyner, J L et al found that urinary NGAL in the early post-operative period appears to predict the development of AKI and correlate strongly with the future need of RRT.

U.S. Publication 2004/0219603 discloses that urinary NGAL measured within two hours of cardiac surgery was predictive of Acute Renal Failure (ARF) as reflected by serum creatinine peak, which occurs several hours or even days later.

Koyner J. L. et al (2007) (supra) show that for both CyC and NGAL the main increase occurs in the ICU (Intensive Care Unit) phase post CT surgery.

Eijkenboom, J. J. A. et al (2005) Intensive Care Med 31:664-667 show that an increase in Glutathione S-Transferase (GST), excretion following cardiac surgery was not correlated with changes in plasma creatinine and is not associated with clinically relevant renal injury.

Davis, C. L. et al (1999) J Am Soc Nephrol 10: 2396-2402 disclose that urinary GST excretion increased in most patients after CPB, however, this increase was not associated with the development of clinically apparent ARF.

There is a need for a biomarker which predicts elevated blood creatinine levels resulting from an abrupt reduction in kidney function and thus the development of AKI at the earliest stage post CT surgery, ideally at zero hours in the recovery room and prior to transfer to ICU or earlier, namely intraoperatively, so as to enable corrective action to be taken as soon as possible for those patients who develop AKI with the attendant consequences.

Currently no drug therapy is available for counteracting the effects of a reduction in kidney function as seen, for example in post CT surgery. Accordingly, the surgeon and other attending medical professionals will endeavour to reduce the effects of renal ischemia or other causative effect by managing fluid levels and other physiological parameters. However, as indicated above, frequently, if such measures do not prove successful, the patient will require RRT, namely dialysis.

DISCLOSURE OF THE INVENTION

Accordingly, the invention provides in a first aspect a method for predicting a need for Renal Replacement Therapy (RRT) in a patient comprising:

determining a concentration of pi glutathione S transferase (πGST) in a first urine sample from the patient; and wherein a need for RRT is predicted when the GST concentration is determined to be elevated in comparison to a patient without kidney injury.

πGST is also referred to hereinafter as pi GST.

Without being bound by any theoretical explanation of the invention, it is believed that elevated urinary GST concentrations can be used to differentiate between patients with less severe acute kidney injury not likely to require RRT and those for whom RRT, for example peritoneal dialysis, hemofiltration, renal transplantation and the like, will be required.

According to this aspect of the invention, the method may further comprise contacting a urine sample from the patient with a capture molecule for πGST.

By "capture molecule" herein is meant any molecule or portion thereof which binds reversibly or irreversibly to πGST, so that said πGST can be detected in the urine sample.

πGST is also referred to herein as "the biomarker".

The GST can be detected by immunoassay and the capture molecule can be an antibody to πGST.

The antibody may be a monoclonal or a polyclonal antibody which binds to πGST.

For example, the biomarker πGST can be detected using an enzyme immunoassay, more particularly an Enzyme Linked Immunosorbent Assay (ELISA). In this regard, the πGST can be assayed using a commercially available kit marketed by Biotrin International Limited, Dublin, Ireland as PI GST EIA, (Catalogue No. BIO 85) which is a 96 well EIA assay format kit. However, any other conventional assay for detecting πGST can be used.

It will be appreciated that as the biomarker is πGST, an enzyme, then the capture molecule therefor can also be a substrate or co-factor therefor.

Alternatively, πGST can be detected enzymatically.

Furthermore, πGST can be detected by a point-of-care assay.

A point-of-care assay will typically be performed on a urine sample of less than 500 µl, typically 10 µl or less. In a point-of-care assay in accordance with the invention, the capture medium will be suitably a dip-stick or like device having the capture molecule affixed thereto.

Elevated urinary GST concentrations can persist for days in a patient in need of RRT.

In such a situation, the RRT will generally involve putting the patient on dialysis supplemented, as required, by managing fluid levels and other physiological parameters.

According to a further aspect of the invention there is provided a method for predicting a need for RRT in a patient comprising;

determining a concentration of πGST in two urine samples taken at least 24 hours apart from the patient; and wherein a need for RRT is predicted when the πGST concentration is determined to be elevated in the two urine samples.

The elevated πGST concentration in the urine can, for example, be ≥30 ng/ml, ≥60 ng/ml, ≥70 ng/ml, ≥80 ng/ml, ≥ or 90 ng/ml or more.

The cause of the underlying renal dysfunction in the patient for whom RRT is predicted can, for example, be such that the patient is affected by an age-related condition, burns, pre-existing chronic kidney disease, reduced effective arterial volume, volume depletion, nephrotic syndrome, congestive heart failure, cirrhosis, sepsis, type I diabetes, type II diabetes, obesity, inflammation, surgery, being a solid organ transplant recipient, being an allogenic bone marrow transplant recipient, mechanical ventilation and/or trauma or has taken or has been administered an antibiotic, drug and/or toxin.

The method according to this aspect of the invention can further comprise detecting for the presence of risk factors for RRT in the patient wherein the risk factor is selected from the group consisting of elevated serum creatinine concentration, type I diabetes, type II diabetes, hypertension, dyslipidemia, hyperglycaemia, proteinuria and hypoalbuminemia.

In the following Examples, Example 1 describes one cause of a reduction in kidney function, namely that which frequently occurs in a patient undergoing CT surgery.

The biomarker is detected earlier than 2 hours post CT surgery or earlier than two hours post Cardio-Pulmonary Bypass (CPB).

More particularly, the biomarker is detected at zero hours post CT surgery or CPB.

It will be appreciated that individuals have different urinary biomarker reference baseline levels. Therefore, post-operative or post-treatment results should be considered in relation to the patient's pre-operative or pre-treatment reference baseline biomarker level, as appropriate.

MODES FOR CARRYING OUT THE INVENTION

The invention will be further illustrated by the following Examples and wherein Example 1 is included for reasons of clarity.

EXAMPLE 1

Use of πGST as a Biomarker for AKI in Patients Undergoing CT Surgery

A retrospective study of 68 patients who had undergone elective CT surgery at the University of Chicago Hospital was carried out.

The patients were screened and approached for enrollment. The patients were excluded if they met any of the following criteria:

Pre-existing End Stage Renal Disease (ESRD) (on RRT) or Renal Transplant.

Age <18 years old.

Use of radiocontrast within 24 hours of surgery.

Change in thyroid hormone replacement dose in the last 2 weeks

Change in thyroid chronic corticosteroids dose in the last 2 weeks

Unstable renal function (Δ Serum Creatinine ≥0.2 mg/dl in the last 2 months of Oliguria defined as <400 ml/day).

Urine and blood samples were collected and stored.

The urine samples were tested for the presence of πGST using the aforementioned πGST EIA available from Biotrin International Limited (Catalogue Number BIO85).

Serum Creatinine (SCr) was measured using the Jaffé Method in a manner known per se on a Beckman Unicel DxC 600 autoanalyser (Beckman Coulter, Fullerton, Calif., USA).

AKI was determined by change in SCr as defined as:

An abrupt (within 48 hours) reduction in kidney function currently defined as 1) absolute increase in serum creatinine of more than or equal to 0.3 mg/dl (≥26.4 µmol/l); or 2) a percentage increase in serum creatinine of more than or equal to 50% (1.5-fold from baseline).

This definition is consistent with the usual definition used, for example, by Mehta, R. L., et al (2007) Critical Care; 11: R31.

Figure 1:
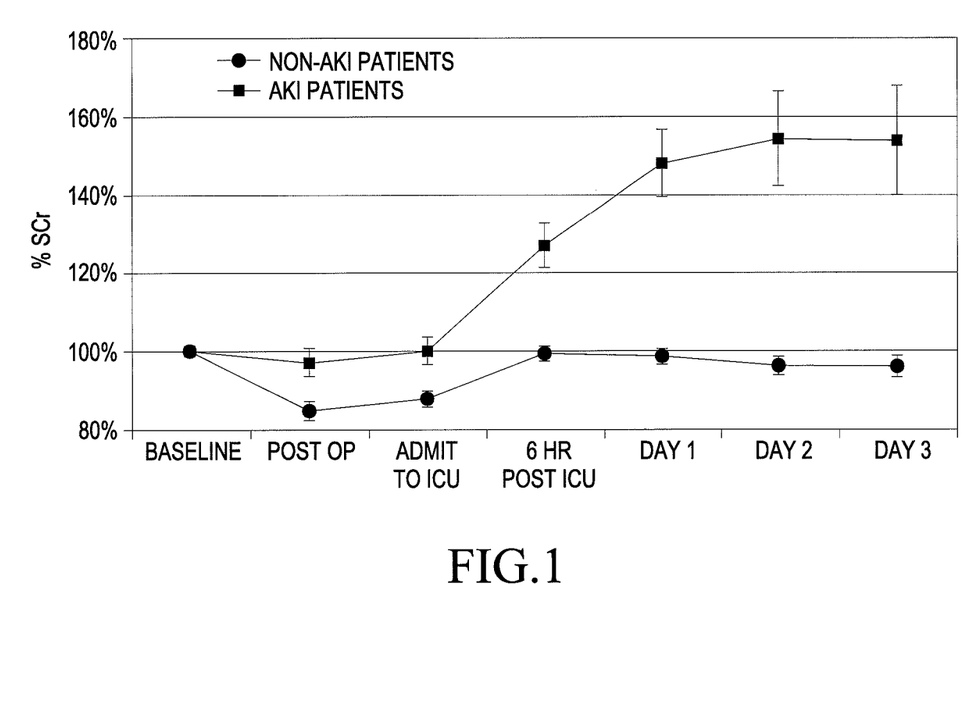
FIG. 1 is a graph of % change in Serum Creatinine (SCr) concentration from baseline versus time as described in Example 1.
Figure 2:
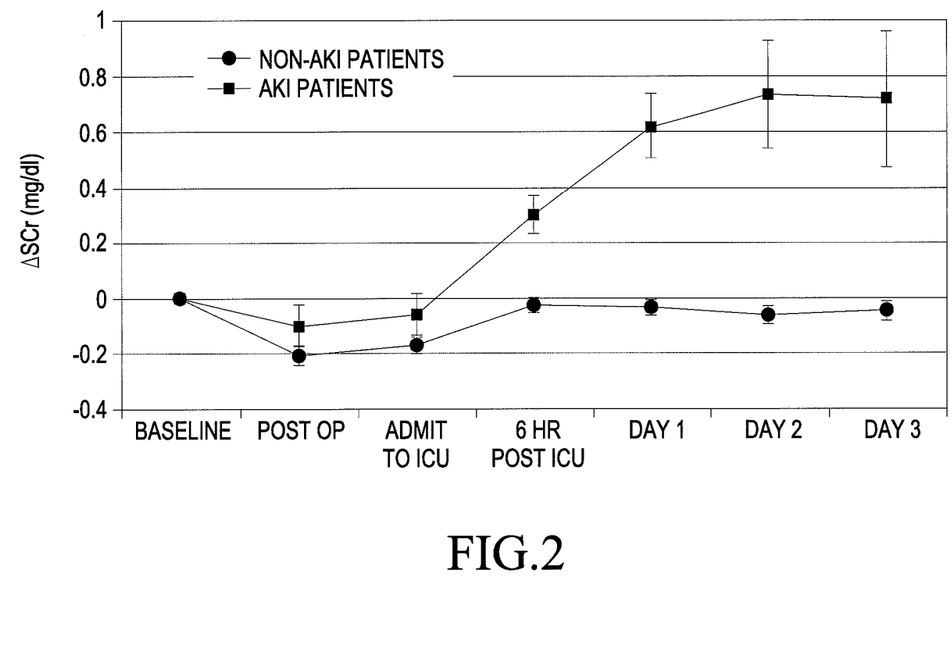
FIG. 2 is a graph of absolute change in SCr concentration (mg/dl) from baseline versus time as described in Example 1.
Figure 3:
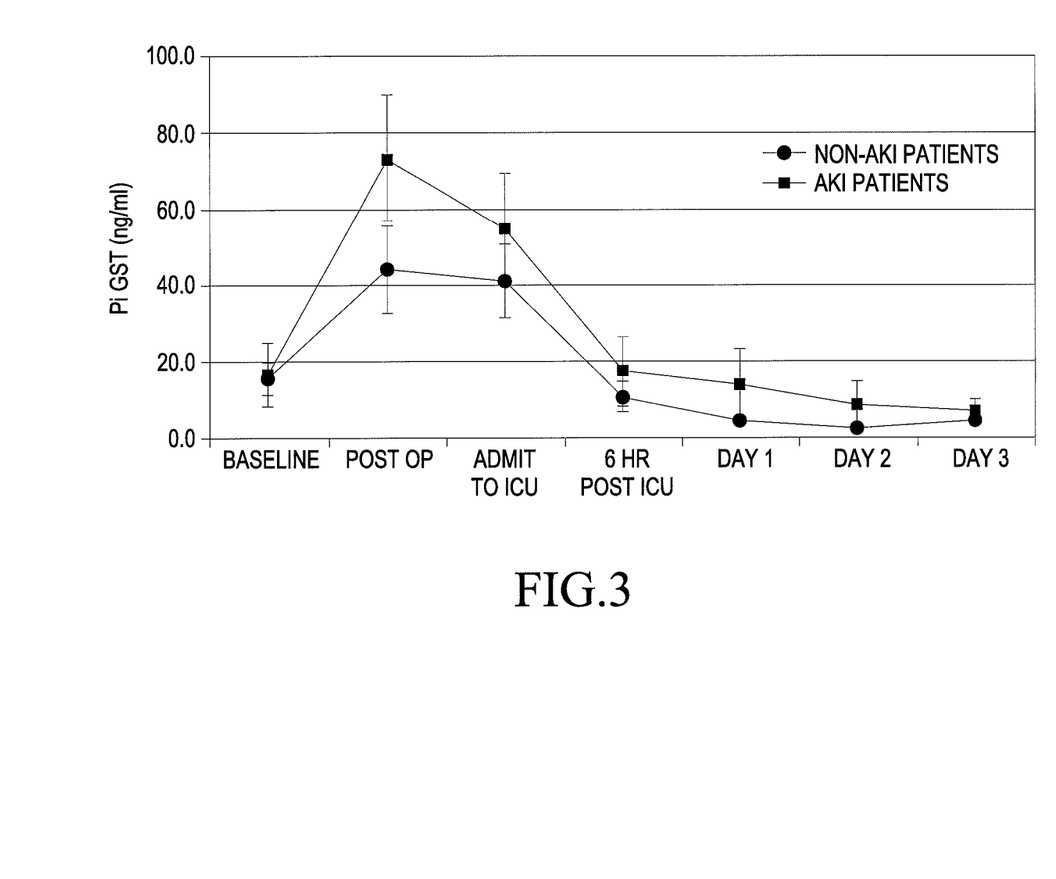
FIG. 3 is a graph of πGST concentration (ng/ml) versus time as described in Example 1.

The results are shown in Table 1 and FIGS. 1-3

TABLE 1

Future Development of AKI (as defined above) by Day 2 post surgery AUC* for ROC** Curves & Sensitivity/Specificity at indicated time points.

| | AUC | Sensitivity | Specificity |
|---|---|---|---|
| Urinary Pi GST Post Op | 0.679 | 63.6% | 72.2% |
| % SCr Post Op | 0.5 | 0.0% | 100.0% |
| % SCr ICU Admit | 0.5 | 0.0% | 100.0% |

TABLE 1-continued

Future Development of AKI (as defined above) by Day 2 post surgery AUC* for ROC** Curves & Sensitivity/Specificity at indicated time points.

|  | AUC | Sensitivity | Specificity |
|---|---|---|---|
| % SCr 6 hr post ICU | 0.56 | 12.0% | 100.0% |
| % SCr Post Op Day 1 | 0.72 | 44.0% | 100.0% |
| ΔSCr Post Op | 0.545 | 9.1% | 100.0% |
| ΔSCr ICU Admit | 0.538 | 7.7% | 100.0% |
| ΔSCr 6 hr post ICU | 0.76 | 52.0% | 100.0% |
| ΔSCr Post Op Day 1 | 0.84 | 68.0% | 100.0% |

*Area under Curve.
*Receiver Operating Characteristic.

FIG. 1 shows the percentage change in SCr from pre-operative baseline values for non-AKI patients (-●-) and AKI patients (-■-). As shown in FIG. 1, the percentage change in SCr does not increase until after the patients have been admitted to ICU. However, as AKI is defined as an increase in SCr of 1.5 fold from baseline, detection of AKI by SCr does not occur until Day 2.

FIG. 2 shows the change in absolute value of SCr from pre-operative baseline values for non-AKI patients (-●-) and AKI patients (-■-). As shown in FIG. 2, a significant increase in SCr concentration does not occur until 6 hours post ICU in AKI patients. As the definition of AKI is an absolute increase in SCr of more than or equal to 0.3 mg/dl, AKI would not be diagnosed until after 6 h Post ICU.

FIG. 3 shows urinary πGST levels following CT surgery for non-AKI patients (-●-) and AKI patients (-■-). As shown in FIG. 3, a significant increase in πGST concentration is observed in Post Op. This indicated that patients could be diagnosed with AKI before they are admitted to ICU. Although an increase in πGST is observed in non-AKI patients, it is significantly lower than AKI patient πGST levels, allowing diagnosis of AKI.

Significantly elevated levels of πGST are detected post-op, namely at zero hours.

Analysis of the data shows that πGST is a good early indicator of patients that will develop AKI by day 2 post surgery.

EXAMPLE 2

Use of πGST as a Biomarker for a Requirement for RRT Patients Undergoing CT Surgery A study was carried out on the 68 patients, the subject of Example 1, using the same methodology for the detection of SCr and πGST.

Seven patients out of the 68 patients tested required RRT. The results are shown in Table 2.

TABLE 2

|  | Baseline Creatinine (mg/dL) | Creatinine at RRT (mg/dL) | Hours in ICU prior to RRT | Indication |
|---|---|---|---|---|
| 1 | 5.03 | 5.4 | 25.3 | Refractory Hyperkalemia (6.0), |
| 2 | 1.49 1.36 post-op | 3.48 | 51.2 | Oliguria Anuria, Elevated creatinine, Shock |
| 3 | 1.3 | 1.42 | 21.6 | Volume overload, Hypoxia, Oliguria, Hemodynamic instability *AKI not diagnosed using current SCr measures* |
| 4 | 1.2 | 3.79 | 26.8 | Lactic Acidosis Oliguria, Shock, Elevated creatinine |
| 5 | 0.99 | 1.28 | 3 | Lactic Acidosis Anuria, Shock, *AKI not diagnosed using current SCr measures* |
| 6 | 1.19 | 1.74 | 5.3 | Anuria, Shock (3 pressors), Volume overload. Acidosis |
| 7 | 1.66 | 2.8 | 81 | Volume overload, pulmonary edema. Shock |

The time point at which patients requiring RRT would be first diagnosed is shown in Table 3.

TABLE 3

| | SCr increase ≥150% | | | | | SCr increase ≥0.3 mg/dL | | | | | Pi GST >90 ng/ml | | | | |
|---|---|---|---|---|---|---|---|---|---|---|---|---|---|---|---|
| | Post-op | Admit to ICU | 6 hr post ICU | Day 1 | Day 2 | Post-op | Admit to ICU | 6 hr post ICU | Day 1 | Day 2 | Post-op | Admit to ICU | 6 hr post ICU | Dat 1 | Day 2 |
| 1 |  |  |  |  |  |  |  | Pos |  |  | Pos |  |  |  |  |
| 2 |  |  | Pos |  |  |  |  |  | Pos |  | Pos |  |  |  |  |
| 3 |  |  |  |  |  |  |  |  |  |  | Pos |  |  |  |  |
| 4 |  | Pos |  |  |  |  |  | Pos |  |  | Pos |  |  |  |  |
| 5 |  |  |  |  |  |  | Pos |  |  |  | * |  | Pos |  |  |
| 6 |  |  | Pos |  |  |  | Pos |  |  |  | Pos |  |  |  |  |
| 7 |  |  |  |  |  |  |  |  |  | Pos |  |  |  |  |  |

* No sample available for testing

Table 4 shows the sensitivity and specificity of πGST to detect RRT as summarised therein

TABLE 4

|  | Cut off | Time point |  | No RRT | RRT |
|---|---|---|---|---|---|
| As determined by Pi GST concentration | | | | | |
| # patients/group | 90 ng/ml | Post-op | No AKI | 43 | 1 |
|  |  |  | AKI | 9 | 5 |
| Sensitivity: 83% | | | Specificity: 83% | | |
| As determined by % SCr increase | | | | | |
| # patients/group | 50% | Post-op | No AKI | 49 | 5 |
|  |  |  | AKI | 0 | 0 |
| Sensitivity: 0% | | | Specificity: 100% | | |

TABLE 4-continued

| | Cut off | Time point | | No RRT | RRT |
|---|---|---|---|---|---|
| # patients/group | 50% | Admit to ICU | No AKI | 60 | 7 |
| | | | AKI | 0 | 0 |
| Sensitivity: 0% | | | Specificity: 100% | | |
| # patients/group | 50% | 6 hr post ICU admit | No AKI | 56 | 5 |
| | | | AKI | 2 | 1 |
| Sensitivity: 17% | | | Specificity: 97% | | |
| # patients/group | 50% | Day 1 | No AKI | 51 | 4 |
| | | | AKI | 8 | 3 |
| Sensitivity: 43% | | | Specificity: 86% | | |
| # patients/group | 50% | Day 2 | No AKI | 55 | 4 |
| | | | AKI | 4 | 3 |
| Sensitivity: 43% | | | Specificity: 93% | | |
| As determined by increase of 0.3 mg/dl in SCr | | | | | |
| # patients/group | 0.3 mg/dl | Post-op | No AKI | 47 | 5 |
| | | | AKI | 2 | 0 |
| Sensitivity: 0% | | | Specificity: 96% | | |
| # patients/group | 0.3 mg/dl | Admit to ICU | No AKI | 58 | 5 |
| | | | AKI | 2 | 2 |
| Sensitivity: 29% | | | Specificity: 97% | | |
| # patients/group | 0.3 mg/dl | 6 hr post ICU admit | No AKI | 47 | 3 |
| | | | AKI | 11 | 3 |
| Sensitivity: 50% | | | Specificity: 81% | | |
| # patients/group | 0.3 mg/dl | Day 1 | No AKI | 41 | 3 |
| | | | AKI | 18 | 4 |
| Sensitivity: 57% | | | Specificity: 69% | | |
| # patients/group | 0.3 mg/dl | Day 2 | No AKI | 45 | 3 |
| | | | AKI | 14 | 4 |
| Sensitivity: 57% | | | Specificity: 76% | | |

Figure 4:
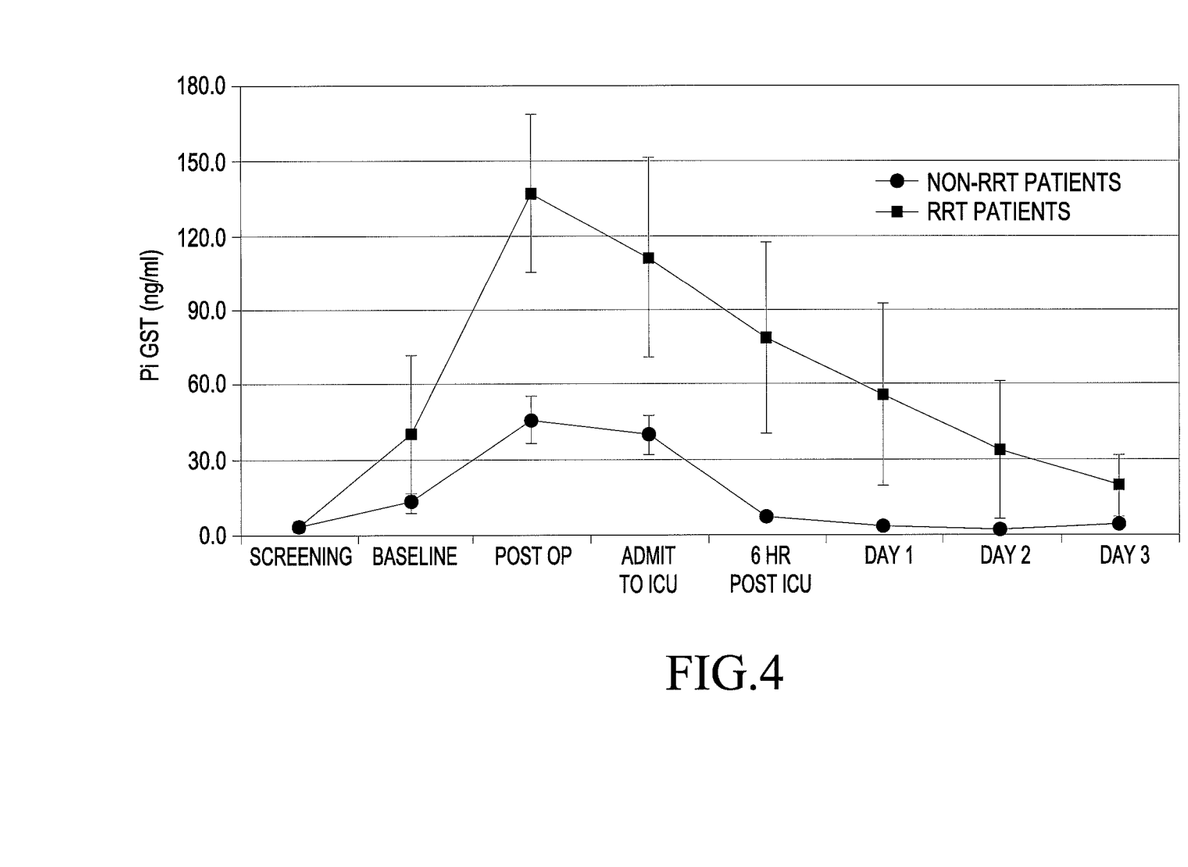
FIG. 4 is a graph of πGST concentration (ng/ml) versus time as described in Example 2.
Figure 5:
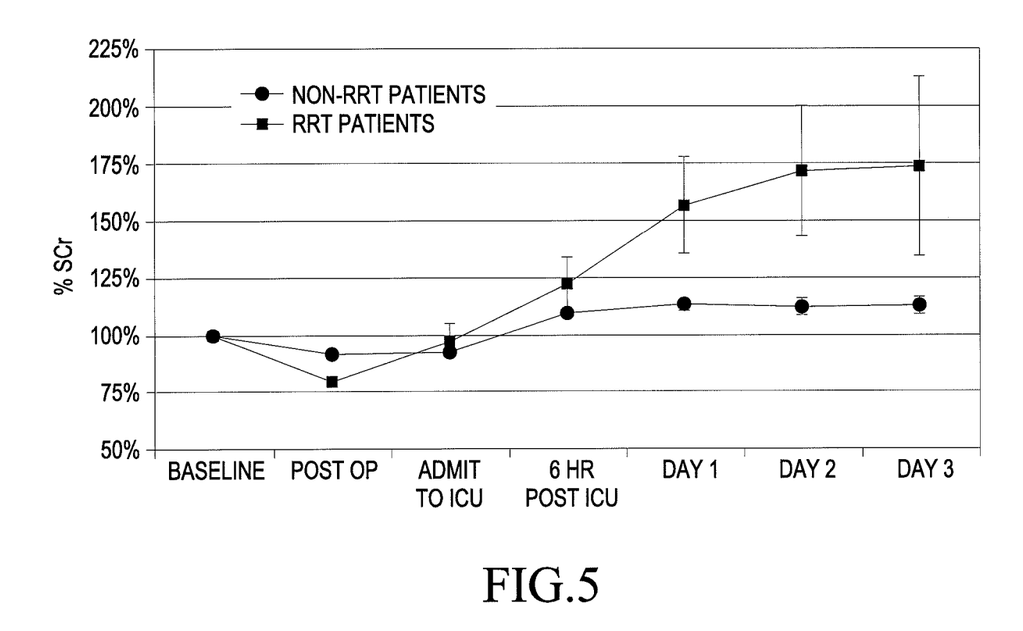
FIG. 5 is a graph of SCr concentration as % of baseline value versus time as described in Example 2.
Figure 6:
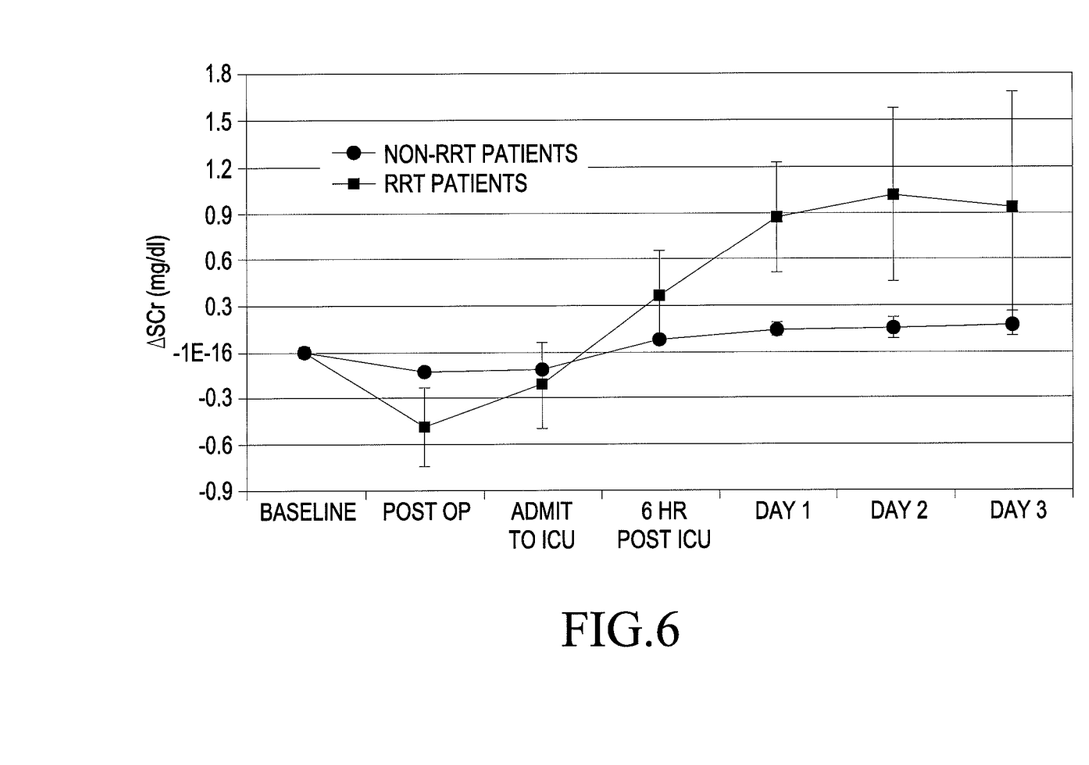
FIG. 6 is a graph of absolute change in SCr concentration from baseline (mg/dl) versus time as described in Example 2.

The results are also depicted in FIGS. 4-6.

FIG. 4 shows the variation in urinary πGST post CT surgery for non-RRT patients (-●-) and RRT patients (-■-). It will be noted that the πGST level of RRT Patients is significantly higher than non-RRT Patients at the Post Op time point. FIG. 4 shows a concentration of 135 ng/ml is reached, which is considerably higher than AKI patients shown in FIG. 3 (75 ng/ml). This indicates severe AKI and that RRT is required.

FIG. 5 depicts the variation in percentage SCr from baseline post CT surgery for non-RRT patients (-●-) and RRT patients (-■-). FIG. 5 shows that the percentage change of SCr above baseline is not significantly elevated above 1.5 fold increase (AKI) until Day 2. This indicates that the earliest diagnosis that RRT is required using this technique would be two days following surgery.

FIG. 6 shows the variation in SCr from baseline post CT surgery for non-RRT patients (-●-) and RRT patients (-●-). It will be noted from FIG. 6 that the absolute change in SCr peaked at Day 2, post surgery. At 6 h post ICU a level of 0.3 mg/dl was reached which indicates AKI. Higher concentrations of SCr were measured at Day 1 and Day 2 indicating severe AKI and a need for RRT. Using this method, RRT would not begin until one day after surgery.

From FIG. 3 and FIG. 4 a relationship is evident between the concentration of πGST and the damage incurred to the patients' kidneys. A πGST concentration of 300%-500% relative to baseline indicates AKI. However, a πGST concentration greater than 500% indicates severe AKI and a requirement for RRT.

The results show that πGST is a very good early indicator of patients that will require RRT undergoing and post CT surgery.

The above Examples show that πGST can be used to detect elevated blood creatinine, AKI and a requirement for RRT earlier than with current biomarkers used to detect an abrupt reduction in kidney function due to renal ischemia intraoperatively or post CT surgery, with the attendant advantages.

What is claimed is:

1. A method for treating acute kidney injury consisting of:
    determining a concentration of pi glutathione S transferase-(πGST) in a urine sample from a patient; and
    performing Renal Replacement Therapy (RRT) when the πGST concentration is determined to be greater than 500% relative to a baseline in comparison to a patient without kidney injury, thereby indicating severe acute kidney injury and a requirement for RRT,
    wherein said patient has not undergone renal transplantation.

2. A method according to claim 1, further comprising contacting a urine sample from the patient with a capture molecule for πGST.

3. A method according to claim 1 or 2, wherein πGST is detected by immunoassay.

4. A method according to claim 3, wherein the capture molecule is an antibody to πGST.

5. A method according to claim 1 or 2, wherein πGST is detected enzymatically.

6. A method according to claim 1, wherein πGST is detected by a point-of-care assay.

7. A method for treating acute kidney injury consisting of
    determining a concentration of πGST in two urine samples taken at least 24 hours apart from a patient; and
    performing Renal Replacement Therapy (RRT) when the πGST concentration is determined to be greater than 500% relative to a baseline in the two urine samples, thereby indicating severe acute kidney injury and a requirement for RRT,
    wherein said patient has not undergone transplantation.

8. A method according to claim 1 or 7, wherein the patient is affected by an age-related condition, burns, pre-existing chronic kidney disease, reduced effective arterial volume, volume depletion, nephrotic syndrome, congestive heart failure, cirrhosis, sepsis, type I diabetes, type II diabetes, obesity, inflammation, surgery, being a non-renal solid organ transplant recipient, being an allogenic bone marrow transplant recipient, mechanical ventilation and/or trauma or has taken or has been administered an antibiotic, drug and/or toxin.

9. A method according to claim 1 or 7, further comprising detecting for the presence of risk factors for RRT in the patient wherein the risk factor is selected from the group consisting of elevated serum creatinine concentration, type I diabetes, type II diabetes, hypertension, dyslipidemia, hyperglycaemia, proteinuria and hypoalbuminemia.

* * * * *